US007688941B2

(12) United States Patent
Thoms (10) Patent No.: US 7,688,941 B2
(45) Date of Patent: Mar. 30, 2010

(54) METHOD FOR DETERMINING THE SET RELATIVE POSITION OF A PATIENT IN DENTAL PANORAMA X-RAY APPARATUS

(75) Inventor: Michael Thoms, Bietigheim-Bissingen (DE)

(73) Assignee: Duerr Dental GmbH & Co. KG, Bietigheim-Bissengn (DE)

( * ) Notice: Subject to any disclaimer, the term of this patent is extended or adjusted under 35 U.S.C. 154(b) by 266 days.

(21) Appl. No.: 11/661,225

(22) PCT Filed: Jul. 12, 2005

(86) PCT No.: PCT/EP2005/007510

§ 371 (c)(1),
(2), (4) Date: Feb. 12, 2008

(87) PCT Pub. No.: WO2006/024342

PCT Pub. Date: Mar. 9, 2006

(65) Prior Publication Data

US 2008/0299511 A1 Dec. 4, 2008

(30) Foreign Application Priority Data

Aug. 27, 2004 (DE) ........................ 10 2004 041 440

(51) Int. Cl.
*A61B 6/14* (2006.01)
*A61B 6/04* (2006.01)

(52) U.S. Cl. ........................ 378/38; 378/195; 378/205
(58) Field of Classification Search ............. 378/38–40, 378/195, 205, 208
See application file for complete search history.

(56) References Cited

U.S. PATENT DOCUMENTS

| 4,229,656 | A |   | 10/1980 | Iversen et al. |         |
|-----------|---|---|---------|----------------|---------|
| 4,599,739 | A | * | 7/1986  | Nishikawa et al. | 378/39 |
| 4,661,967 | A | * | 4/1987  | Nishikawa      | 378/39  |
| 4,741,007 | A | * | 4/1988  | Virta et al.   | 378/39  |

(Continued)

FOREIGN PATENT DOCUMENTS

DE 3808009 A1 9/1988

(Continued)

*Primary Examiner*—Irakli Kiknadze
*Assistant Examiner*—Thomas R Artman
(74) *Attorney, Agent, or Firm*—Factor & Lake, Ltd.

(57) ABSTRACT

The invention relates to a method for determining the set relative position of a patient in a dental panorama X-ray apparatus during which the curvature of a front area of a dental arch of a patient is determined. Set position coordinates for the patient are calculated based on this curvature and on a projection arch surface. In addition, the curvature of a middle area and/or of a rear area of the dental arch is determined and is taken into consideration during the calculation of the position coordinates. During a method for determining the set path of a diagnostic unit, the curvature of a front area of a dental arch of a patient is determined and is fixed at a location in the X-ray apparatus located within the space scanned by an X-ray source and by a detector unit. In addition, the curvature of a middle area and/or of a rear area of the dental arch is determined and a set path curve for the diagnostic unit is calculated based on the measured curvatures. The invention also relates to a device suited for carrying out the aforementioned method.

12 Claims, 5 Drawing Sheets

U.S. PATENT DOCUMENTS

| | | | |
|---|---|---|---|
| 4,782,503 A * | 11/1988 | Molitor et al. | 378/169 |
| 4,907,251 A | 3/1990 | Mork et al. | |
| 5,195,114 A | 3/1993 | Sairenji et al. | |
| 5,692,027 A | 11/1997 | Yoshimura | |
| 5,828,721 A * | 10/1998 | Schulze-Ganzlin et al. | 378/38 |
| 5,921,927 A * | 7/1999 | McArdle | 600/425 |
| 5,989,023 A * | 11/1999 | Summer et al. | 433/69 |
| 6,289,074 B1 * | 9/2001 | Arai et al. | 378/4 |
| 6,493,415 B1 * | 12/2002 | Arai et al. | 378/4 |
| 7,039,156 B2 * | 5/2006 | Arai et al. | 378/39 |
| 7,421,059 B2 * | 9/2008 | Suzuki et al. | 378/39 |
| 7,545,372 B2 * | 6/2009 | Kopelman et al. | 345/419 |
| 2005/0031086 A1 | 2/2005 | Dalpiaz et al. | |

FOREIGN PATENT DOCUMENTS

WO  02065918A A1  8/2002

* cited by examiner

METHOD FOR DETERMINING THE SET RELATIVE POSITION OF A PATIENT IN DENTAL PANORAMA X-RAY APPARATUS

RELATED APPLICATIONS

This application claims the filing benefit of International Patent Application No. PCT/EP2005/007510, filed Jul. 12, 2005, which claims the filing benefit of German Patent Application No. 10 2004 041 440.8 filed Aug. 24, 2004, the contents of which are incorporated herein by reference.

TECHNICAL FIELD

The present invention relates to a method for determining the set relative position of a patient in a dental panorama X-ray apparatus, wherein
the curvature of a front region of a patient's dental arch is established; and
based thereon and on a projection arch surface of the panorama X-ray apparatus, set position coordinates for the patient's jaw are calculated.

The present invention further relates to a method for determining the set path on which a dental panorama X-ray apparatus is moved with respect to a patient, wherein
the curvature of a front region of a patient's dental arch is established; and
the patient's dental arch is fixed at a location in the panorama X-ray apparatus located within the space scanned by an X-ray source and a detector unit connected rigidly thereto.

The present invention also relates to a device for determining the set relative position of a patient in a dental panorama X-ray apparatus or the set path of a diagnostic unit with respect to the patient's jaw fixed in a panorama X-ray apparatus, comprising
a sensor unit which cooperates with the patient's teeth in the front region of the jaw and which provides a jaw form signal characteristic of the position of the patient's teeth; and
a computing unit to which the jaw form signal from the sensor unit is applied and which calculates, based thereon and on the path of an X-ray source and a detector unit of the panorama X-ray apparatus, which detector unit determines the projection arch surface of the panorama X-ray apparatus, set position coordinates for the patient's jaw.

BACKGROUND OF THE INVENTION

A projection arch surface (or "projection arch" for short) describes the arch surface that is clearly mapped in the resultant X-ray image of a panorama X-ray apparatus. In other words, the X-ray image displays the patient's tissue that is located in the projection arch surface when the X-ray is taken.

During the taking of a dental panorama X-ray image, the patient's head is located between an X-ray source and an X-ray detector which circumscribe the patient's head in a curved path. The X-ray source and the detector unit are for this purpose generally rotated, at a uniform distance from one another in a horizontal plane, about a vertical axis of rotation extended, in turn, along a specific path during the rotation process. The ideal course of this path results from the geometry of a patient's dental arch. In the region of the front teeth, the dental arch displays a marked curvature, whereas in the region of the central or rear teeth the curvature is less pronounced.

As the X-ray source and the detector unit move around the patient's head, a large number of individual photographs are taken which are combined by a suitable computing unit to form an overall image.

There is to be allocated to each individual photograph a narrow, planar projection region in which the patient's tissue through which the X-rays pass is clearly mapped. To put it simply, relatively narrow horizontal regions of individual images are therefore combined in each case to form the panorama X-ray image, the axis of rotation of the X-ray source and detector unit moving in accordance with a standard jaw shape.

The projection arch surface of the panorama X-ray apparatus is obtained from the correspondingly combined horizontal regions of the projection planes of the respective individual images or image strips. Overall, the projection arch surface of the panorama X-ray apparatus results from the path in which the X-ray source and the detector unit circumscribe the patient's head and which generally has to be set manually or on the basis of data from a database.

There are also further recording settings of the dental panorama X-ray apparatus to be carried out including, inter alia, the tube voltage, the exposure time, the beam current and the beam cross-section as parameters for the X-ray source.

In order for the resultant X-ray image also to display the desired regions of the patient, the patient has to be positioned in a specific set relative position in the panorama X-ray apparatus, in which position the largest possible area of the patient's dental arch coincides with the projection arch surface.

The positioning of the patient, like the adjusting of the panorama X-ray apparatus is conventionally carried out manually. The panorama X-ray apparatus accordingly has a bite-on-holder that the patient bites into. The patient is then positioned, usually using an optical device, in such a way that the plane between his upper and his lower jaw extends horizontally. The projection arch is then manually adjusted in accordance with the patient's dental arch visually detected by the operator, and the patient is brought between the X-ray source and the X-ray detector vertically and horizontally into a position such that the projection arch surface of the panorama X-ray apparatus extends as precisely as possible through the roots of the patient's teeth.

The above-mentioned manual adjustments are firstly very time-consuming and secondly highly prone to error. More than half of panorama X-ray photographs taken are inadequate, as the position arch surface does not extend as desired through the roots of the teeth which are therefore mapped unclearly.

A reduction in the sources of error was achieved by a device of the type mentioned at the outset such as is described in DE 38 08 009 C2. In this device, the position of the patient's incisors and/or canines is established using various types of sensor. The relative positions of the detected teeth with respect to one another are used as the basis for determining the set relative position of the patient in the panorama X-ray apparatus. In order to determine the patient's dental arch, use is made of a database in which physiological patient data is stored. From this database there is allocated to the patient to be examined a dental arch geometry corresponding as closely as possible to the shape of the dental arch established from the positions of the incisors and/or canines of the patient to be examined.

As merely the patient's incisors and/or canines are detected for determining the patient's dental arch, there can be allocated to the patient from the database a dental arch geometry which differs from his actual dental arch shape and, in particular, takes in the central and rear jaw regions a different course from that actually found in the patient.

It can therefore occur that the X-ray image taken does not represent the region of the patient's molars and grinders with sufficient clarity and is unsuitable for subsequent diagnosis by the dentist performing the treatment.

The present invention is directed to addressing these and other matters.

SUMMARY OF THE INVENTION

An object of the present invention is to provide a method and a device of the type mentioned at the outset in which the set relative position of a patient in a dental panorama X-ray apparatus or the set path on which a dental panorama X-ray apparatus is moved with respect to a patient can be established more effectively.

With regard to the method, this object may be achieved, based on the set relative position, in that in addition, the curvature of a central region and/or rear region of the patient's dental arch is established and taken into account in the calculation of the set position coordinates for the jaw.

Based on the set path on which a dental panorama X-ray apparatus is moved with respect to a patient, the above-mentioned object may be achieved in that in addition, the curvature of a central region and/or rear region of the patient's dental arch is established; and, based on the measure curvatures of the front and central and/or rear region of the dental arch, a set path curve is calculated for the diagnostic unit formed by the X-ray source and detector unit.

In regard to the device, the aforementioned object may be achieved in that the sensor unit additionally cooperates with the patient's teeth in the central region and/or rear region of the jaw.

By additionally establishing the curvature of the central and/or rear region of the patient's dental arch or as a result of the fact that the sensor unit cooperates with the central and/or the rear region of the jaw, the entire geometry of the patient's dental arch can be determined with a high degree of precision. There is accordingly no need to access physiological patient data stored in a database when calculating the patient's set position coordinates. Error-prone visual determination of the geometry of the patient's dental arch is now also superfluous. The patient's set relative position is calculated on the basis of a measured geometry of the patient's dental arch corresponding closely to the actual dental arch geometry. As a result, the calculated set relative position of the patient is such that the projection arch surface of the panorama X-ray apparatus coincides, when taking the panorama X-ray image, with the patient's dental arch with a high degree of precision.

The calculation of the set path curve for the diagnostic unit formed by the X-ray source and detector unit on the basis of the measured curvatures of the front and central and/or rear region allows the projection arch surface to be adapted to the actual geometry of the patient's dental arch.

Other advantageous embodiments of the device according to the invention are described in the dependent claims.

It is to be understood that the aspects and objects of the present invention described above may be combinable and that other advantages and aspects of the present invention will become apparent upon reading the following description of the drawings and detailed description of the invention.

DETAILED DESCRIPTION OF THE PRESENT INVENTION

Figure 1:
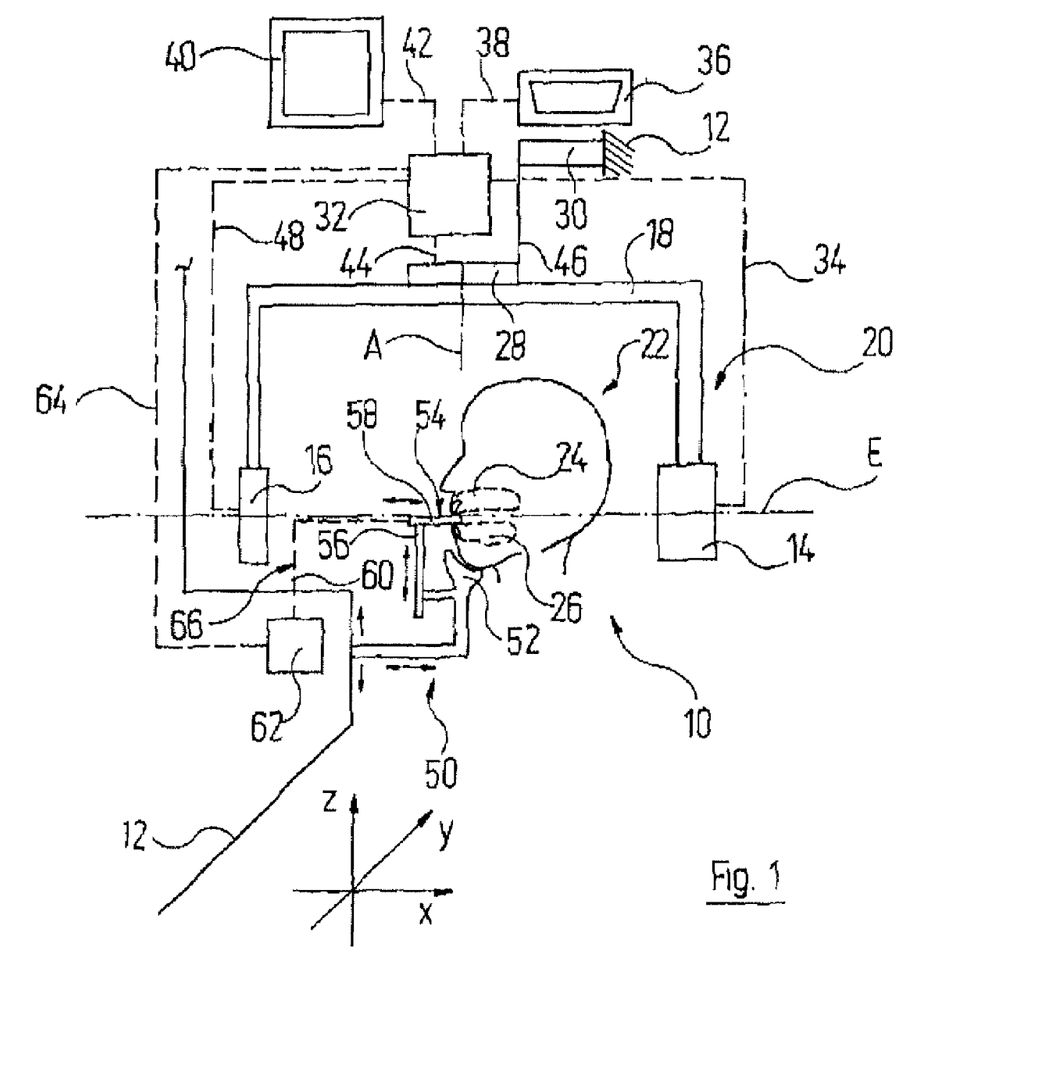
FIG. 1 is a side view of a dental panorama X-ray apparatus with a first embodiment of a device for determining the set relative position of a patient or the set path of a diagnostic unit.

FIG. 1 shows a dental panorama X-ray apparatus 10 with a frame 12, comprising an X-ray source 14 and a detector unit in the form of a CCD sensor 16. The X-ray source and detector unit are rigidly connected to each other via a rotary arm 18 so as to be able to rotate about a vertical axis A, the X-ray source and detector unit opposing each other at the same height. E denotes the recording plane which is located perpendicularly on the axis of rotation A and intersects the centre of the CCD sensor 16 and the centre of the window, located at the same level, of the X-ray source 14. An x, y, z coordinate system indicated in FIG. 1 is secured to the frame. Its z axis extends parallel to the axis of rotation A, its x-y plane is parallel to the recording plane E. The X-ray source 14, the CCD sensor 16 and the rotary arm 18 together form a diagnostic unit 20.

A patient whose jaw is to be X-rayed by the panorama X-ray apparatus is positioned for the recording at the level of the X-ray source 14 or the CCD sensor 16 in such a way that X-rays generated by the X-ray source 14 pass through his head 22, or more precisely his upper jaw 24 and his lower jaw 26, before striking the CCD sensor 16.

The rotary arm 18 is mounted above the patient so as to be rotatable about the vertical axis of rotation A and can be rotated using a drive motor 28. The axis of rotation A can in this regard additionally be moved horizontally by a coordinate drive 30 in at least one direction, preferably in two independent directions. When taking a panorama X-ray photograph, the X-ray source 14 and the CCD sensor 16 thus circumscribe the patient's head 22 on a specific curved path located in the horizontal plane E.

The recording settings, such as the tube voltage, exposure time, beam current or beam cross-section, are transmitted to the X-ray source 14 by a computing unit 32 via a data transmission line 34.

The path of the axis of rotation A and the recording settings of the X-ray source 14 can be input into the computing unit 32 via a keypad 36 communicating with the computing unit 32 by way of a data transmission line 38. The input commands are displayed on a display monitor 40 which receives corresponding signals from the computing unit 32 via a data transmission line 42.

The computing unit 32 controls the drive motor 28 via a line 44 and the coordinate drive 30 via a line 46.

The computing unit 32 also receives the output signals from the CCD sensor 16 via a data transmission line 48 and optionally transmits to the CCD sensor control commands such as read-out, integration time and delete clock pulses.

Overall, the computing unit 32 acts as the central control unit which coordinates the recording of the panorama image, processes the signals received from the CCD sensor 16 and converts them into a visible image which is displayed on the monitor 40.

During the recording, the patient's head 22 is fixed by a positioning device 50 and brought into a corresponding set position relative to the panorama X-ray apparatus 10 before the X-ray is taken.

The positioning device 50 comprises a chin rest 52 which is attached to the frame 12 so as to be able to move vertically and in two independent horizontal directions and can be fixed after reaching a desired horizontal or vertical position.

The positioning device 50 further comprises a bite-on holder 54 which is connected to the chin rest 52 via a support rod 56, which is vertically adjustable and can be fixed in a desired position, and can itself move in the horizontal plane, along a straight path and can be fixed at this location in a desired position.

The displaceability of the bite-on holder 54 and the support rod 56 is used in this regard to adapt to the relative positions of the individual components 52, 54 and 56 to the patient's physiology.

The positions of the bite-on holder 54 and the support rod 56 are first adjusted manually by the operator so as to allow the patient to bite the bite-on holder 54, while his chin rests on the chin rest 52.

Overall, the vertical position of the positioning device 50 is then adjusted in such a way that the patient's jaw region 24, 26 is located at the level of the X-ray source 14 and the CCD sensor 16.

Known positioning aids, usually optical systems, ensure that the plane extends horizontally between the patient's upper jaw 24 and lower jaw 26.

Overall, the positioning device 50 is therefore configured in such a way that it can be adjusted in all necessary directions to a patient's individual head and jaw physiology, thus allowing the patient's jaw region 24, 26 to be fixed in a specific relative position with respect to the frame 12.

A bite-on sensor 58 is arranged on the bite-on holder 54. The bite-on sensor is connected via a line 60 to a jaw form identification circuit 62 which generates a jaw form signal from the output signal from the bite-on sensor 58 and transmits it to the computing unit 32 via a data transmission line 64. The bite-on sensor 58 and the jaw form identification circuit 62 together form a jaw form sensor unit 66.

Figure 2A:
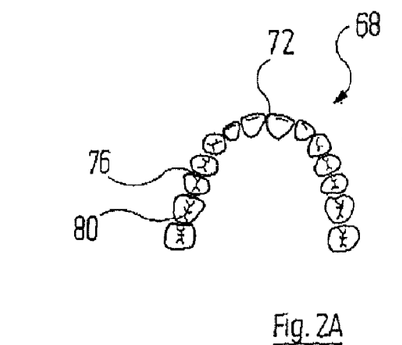
FIGS. 2A and 2B show two examples of differing geometries of a patient's dental arch and are schematic views of the path of the axis of rotation of the X-ray source and detector unit.
Figure 2B:
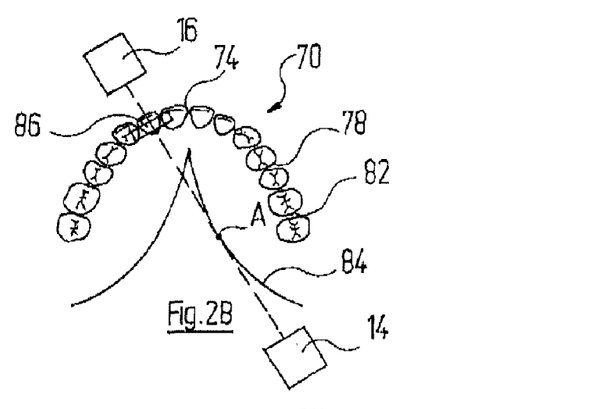

Depending on the physiology of a patient's jaw, the rows of teeth of various patients extend in differing dental arches. FIG. 2 shows, as examples of various dental arch geometries, a relatively narrow dental arch 68 (FIG. 2A) and a relatively wide dental arch 70 (FIG. 2B), each on the basis of an upper-jaw row of teeth.

As may be seen in these figures, the dental arches 68, 70 display a more marked curvature in the front region 72 and 74, respectively, than in a respective central region 76 and 78 and rear region 80 and 82. By comparison, the central region 76, 78 has a less pronounced curvature and the rear region 80, 82 only a slight curvature.

On rotation of the rotary arm 18, the vertical axis of rotation A thereof is moved synchronously on a curved path which is illustrated schematically in FIG. 2B, using the example of the dental arch 70, and is provided with reference numeral 84. The path 84 of the axis of rotation A corresponds approximately to a downwardly open V with convex legs. This course, which will vary depending on the shape of the dental arch, ensures that the projection plane 86 of each individual image is located within a patient's dental arch 68 or 70, as the distance between the X-ray source 14 and CCD sensor 16 is constant.

Figure 3A:
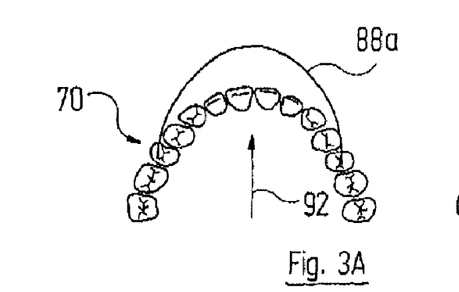
FIGS. 3A and 3B illustrate schematically the change in the relative position of the patient based on the projection arch surface of the panorama X-ray apparatus as shown in FIG. 1.
Figure 3B:
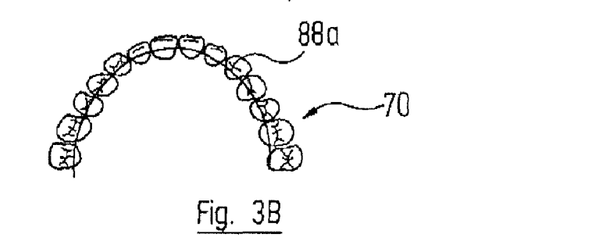

FIGS. 3A and 3B and also 4A and 4B show projection arch surfaces 88a, 88b and 88c in comparison to the dental arch 70 of FIG. 2B. In order to achieve maximum overlap of the projection arch surface 88 and the patient's dental arch 70, it is firstly necessary to establish the actual geometry of the dental arch of the patient to be examined. This is done using the bite-on sensor 58.

Figure 5:
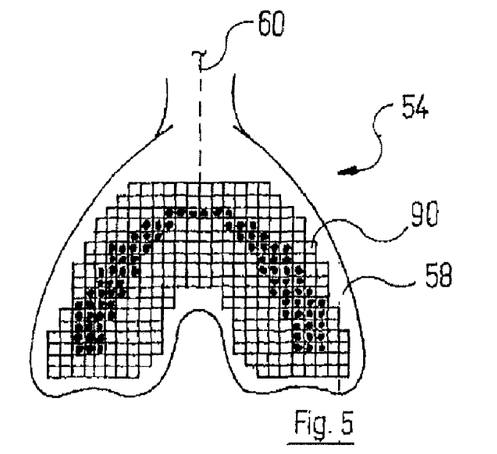
FIG. 5 is a plan view onto a sensor unit of the device as shown in FIG. 1.

FIG. 5 is a view of the side of the bite-on sensor 58 that faces the patient's upper jaw 24.

The bite-on sensor 58 comprises pressure transducers which are arranged on its surface and one of which is denoted in FIG. 5 by reference numeral 90. When a patient bites onto the bite-on holder 54 and therefore onto the bite-on sensor 58 arranged thereon, a large number of pressure transducers 90 are depressed in accordance with the patient's dental arch.

In FIG. 5, the blackened pressure transducers 90 illustrate which pressure transducers 90 would be approximately depressed if a patient having a dental arch 70, as illustrated in FIGS. 2d, 3 and 4, were to bite the bite-on sensor 58.

Each depressed pressure transducer 90 generates a signal which is transmitted to the jaw form identification circuit 62 via the communication line 60. The jaw form identification circuit generates in turn a jaw form signal corresponding to the overall image of the depressed pressure transducer 90.

The foregoing observations concerning the depressed pressure transducers 90 of the bite-on sensor 58, with respect to a patient's upper-jaw teeth, applies accordingly to the patient's lower-jaw teeth. The bite-on sensor 58 therefore comprises, on the side facing the patient's lower-jaw region, pressure transducers 90 which are also arranged on the surface, are depressed, when the patient bites the bite-on sensor 58, by his lower-jaw teeth, and accordingly communicate with the jaw form identification circuit 62.

The depressed pressure transducers 90 therefore face one another for the positioning of the detected teeth, on the basis of which the jaw form identification circuit 62 generates a jaw form signal which corresponds to the patient's dental arch, based on the upper and the lower jaw 24 and 26 respectively, and is taken as a basis in the calculation by the computing unit 32 of the geometry of the patient's dental arch.

The computing unit 32 is then able to compare the projection arch surface defined by the path 84 of the axis of rotation A of the panorama X-ray apparatus 10 (the projection arch surface 88a shown in FIG. 3A should be singled out in this regard) with the shape of the patient's dental arch and bring both shapes into line with each other. This is carried out, for example, in that the central distance square between the dental arch and a standard projection arch which is adjustable for the device is minimised by translations and/or rotations of the dental arch (least square fit).

As a result, the computing unit 32 proposes set position coordinates for the patient's jaw 24, 26, in particular set horizontal coordinates of the chin rest 52. As a result of this adaptation, the patient's dental arch 70 is moved, as illustrated in FIG. 3A, in the direction of arrow 92 until the calculated set horizontal coordinates are reached and the largest possible area of the patient's dental arch 70 overlaps with the projection arch surface 88a. The latter scenario is illustrated in FIG. 3B.

If the patient's dental arch is established remote from the panorama X-ray apparatus 10, for example using a plaster cast, the computing unit 32 calculates the spatial set position coordinates based on the panorama X-ray apparatus 10.

In a development, it is possible for the differing positions of the individual components 52, 54 and 56 to be adjustable using servomotors which transmit actual position signals to the computing unit 32 and are controlled by the computing unit in set positions. The resultant set relative position of the patient can thus also be automatically adjusted.

Figure 4A:
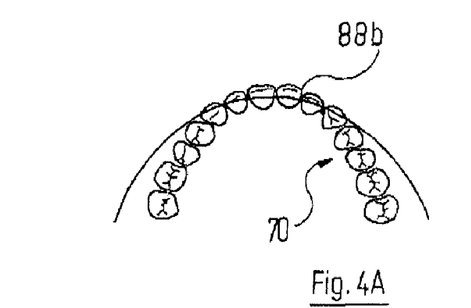
FIGS. 4A and 4B illustrate schematically the adaptation of the projection arch surface of the panorama X-ray apparatus to the geometry of the patient's dental arch.
Figure 4B:
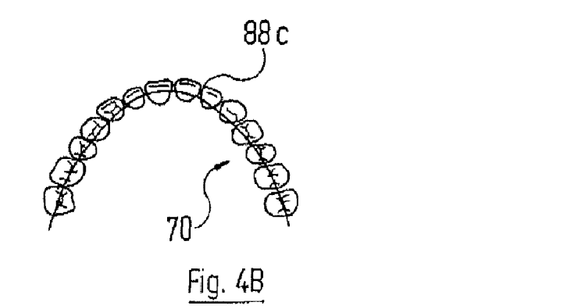

In addition to this adaptation of the patient's relative position to an existing position arch surface, the computing unit 32 is able to calculate the path 84 of the diagnostic unit 20 in such a way that the projection arch surface is changed from a form little suited to the established dental arches of the patient, such as is shown, for example, in FIG. 4A in the form of the projection arch surface 88b, to a projection arch surface is 88c (FIG. 4B) which corresponds to a high degree to the course of the patient's dental arch.

This process of adapting the projection arch surface to the patient's dental arches is, in this case, carried out autonomously by the computing unit 32, the bite-on sensor 58 and the various position indicators and optionally servomotors which cooperate with the components 52, 54, 56, so overall the patient's set relative position and, in particular, the path 84 of the axis of rotation A of the diagnostic unit 20 of the panorama X-ray apparatus 10 are adapted completely automatically.

As may be seen in FIG. 5, the pressure transducers 90 of the bite-on sensor 58 detect, in addition to the front, markedly curved region 74 of the dental arch 70, the respectively less markedly curved central region 78 or the rear region 82, which has little curvature. The shape of the patient's dental arch can thus be established with a high degree of precision in accordance with the actual shape of the patient's dental arch.

The adaptation of the projection arch surface to the geometry of the patient's dental arch is accordingly based on the patient's actual dental arch, so overlapping, individually adapted to a high degree to the patient, of the projection arch surface 88 of the panorama X-ray apparatus 10 and the patient's dental arch 68 or 70 is obtained.

Figure 6:
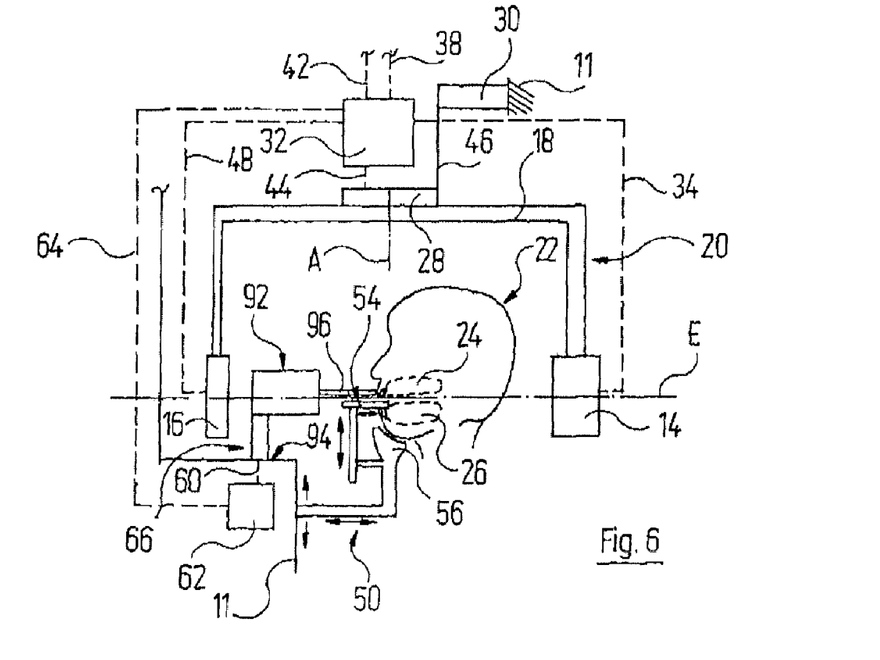
FIG. 6 is a side view of a dental panorama X-ray apparatus with a second embodiment of a device as shown in FIG. 1 with a modified sensor unit.
Figure 7:
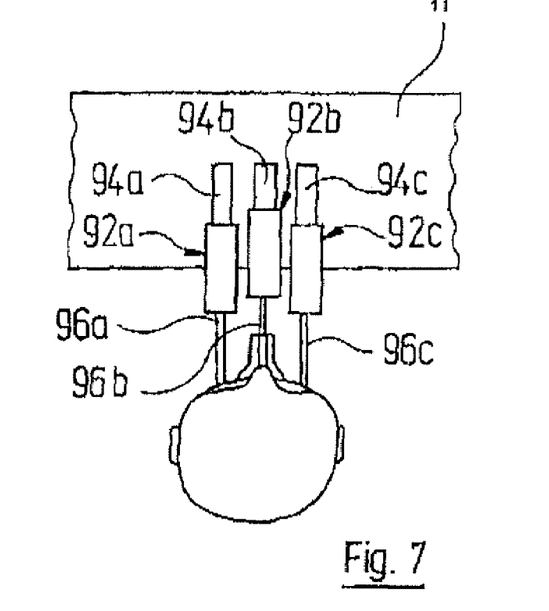
FIG. 7 is a plan view onto the sensor unit of the device as shown in FIG. 6.

FIGS. 6 and 7 show a further embodiment of a device for determining a patient's set relative position in a dental panorama X-ray apparatus or the set path of a diagnostic unit with respect to a patient's jaw held in a panorama X-ray apparatus. In these figures, components corresponding to the embodiment of FIG. 1 are denoted by identical reference numerals.

In contrast to the embodiment of FIG. 1, no sensor is arranged on the bite-on holder 54.

Instead, the jaw form sensor unit 66 comprises a plurality of position indicators 92 which are configured as electromechanical probes and communicate with the jaw form identification circuit 62 via corresponding data transmission lines 60. FIG. 7 is a plan view, by way of example, of three position indicators 92a, 92b, 92c arranged next to one another.

The position indicators 92 can moved horizontally along a rectilinear path 94a, 94b or 94c and fixed in a desired position. The position of a probe tip 96 of a position indicator 92 is transmitted to the jaw form identification circuit 62 via the data transmission line 60.

For establishing the form of the patient's jaw, the jaw form sensor unit 66 is moved toward the patient, who is held in the positioning device 50, until the probe tips 96 of the position indicators 92 contact the outside of the patient's head 22 at the level just above the upper lip. For this purpose, the patient is to be brought beforehand into a corresponding suitable vertical position.

The output signals from the position indicators 92 are passed on to the jaw form identification circuit 62. The jaw form identification circuit 62, in turn, generates a jaw form signal corresponding to a model dental arch which matches the positions of the position indicators 92 and approximates the patient's dental arch.

Once the computing unit 32 has received the jaw form signal via the data transmission line 64, it calculates the patient's set relative position in a manner similar to that described hereinbefore, for example by the least square fit method. The further observations concerning the first embodiment as shown in FIG. 1 to 5 apply accordingly to the second embodiment as shown in FIGS. 6 and 7.

Increasing the number of position indicators 92 allows the precision of the determination of the geometry of the patient's dental arch to be increased.

Figure 8:
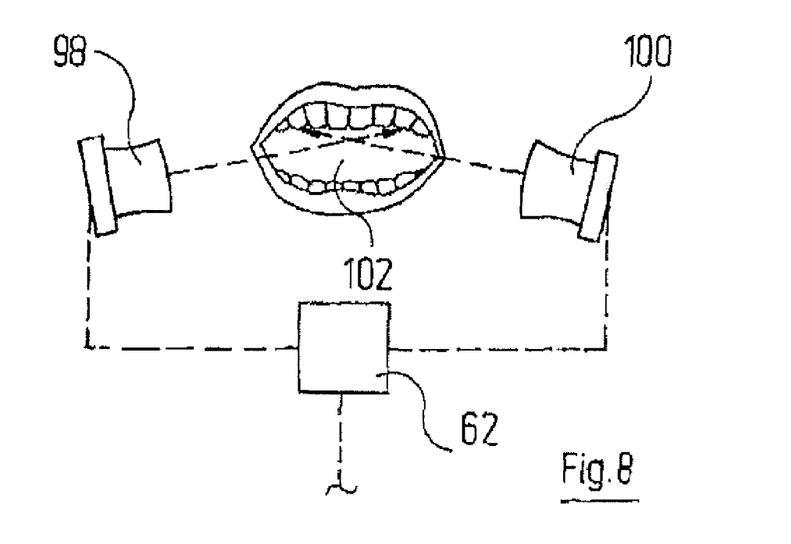
FIG. 8 shows a further modified sensor unit of a third embodiment of a device corresponding to FIG. 1; and, FIG. 9 is a schematic view of a device for determining the set path curve of a diagnostic unit of a panorama X-ray apparatus.

FIG. 8 shows schematically a further embodiment in which components corresponding to the embodiment of FIG. 1 have the same reference numerals.

In this embodiment, the set position of the patient relative to the panorama X-ray apparatus is established in that the geometry of the patient's teeth is determined using two cameras 98 and 100 which detect the patient's mouth cavity 102, and therefore his teeth, from two differing angles. The signals from the cameras 98, 100 are transmitted via corresponding data transmission lines 104 and 106 to the jaw form identification circuit 62 which carries out a suitable image processing algorithm which as a result sends to the computing unit 32 a jaw form signal from which the computing unit calculates the geometry of the patient's dental arch.

The further calculation of the patient's set relative position or the set path of the diagnostic unit 20 of the panorama X-ray apparatus 10 is carried out, again, in accordance with the above-mentioned processes.

Figure 9:
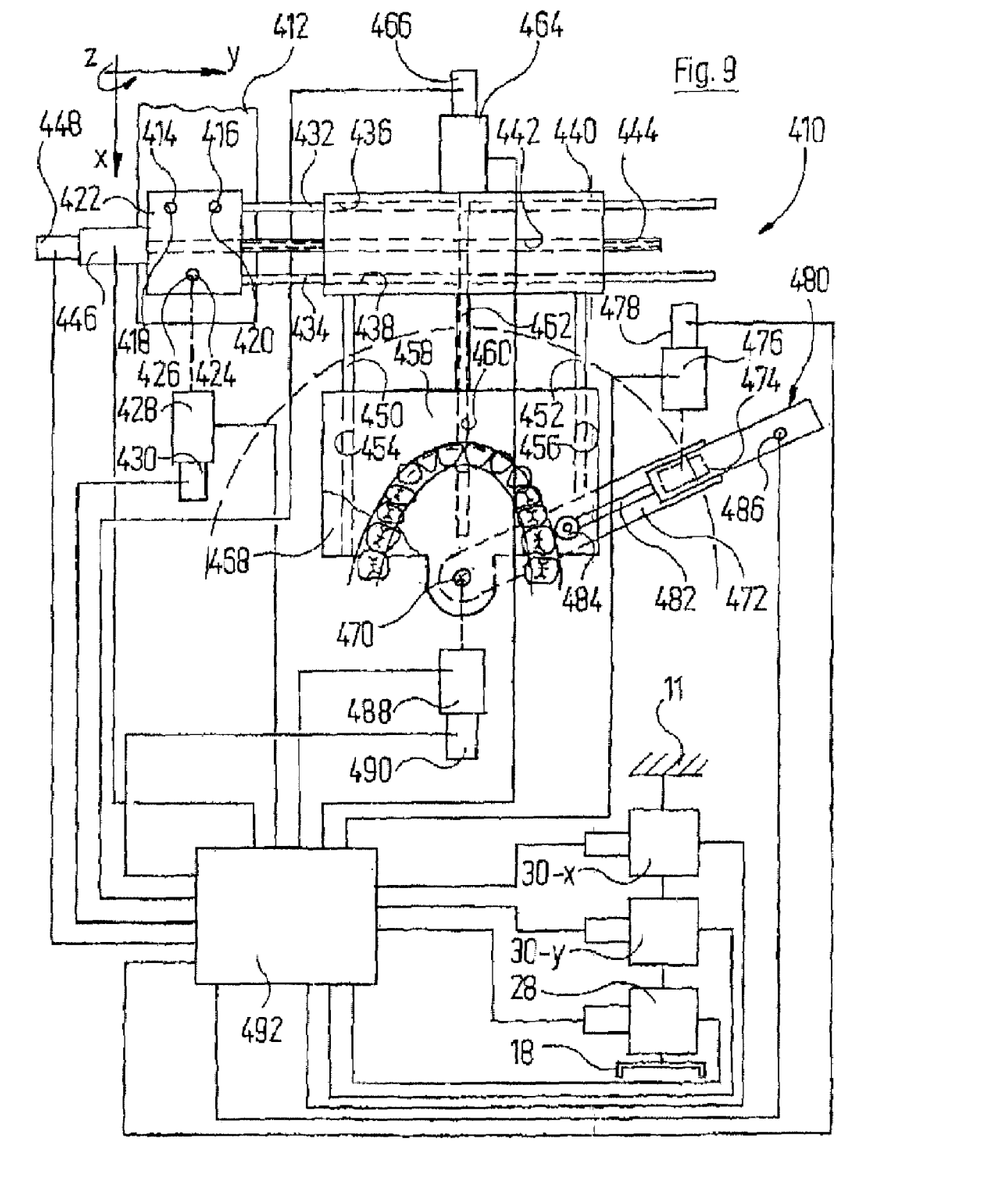

FIG. 9 shows a device, denoted in its entirety by reference numeral 410, which is used to guide in the recording plane a diagnostic unit 20 of a panorama X-ray apparatus 10, which diagnostic unit comprises the X-ray source 14, the CCD sensor 16 and the rotary arm 18, in such a way that the projection arch 88 of the X-ray apparatus 10 corresponds to the dental arch 68, 70 of the patient to be examined.

Carried by a fixed portion 412 of the frame of the X-ray apparatus are two vertical guide rods 414, 416 which are set apart from each other and cooperate with guide holes 418, 420 in a z-shaped carriage 422. Also provided in the z-shaped carriage is a tapped hole 424 in which there passes a threaded spindle 426. The threaded spindle is driven by an electric motor 428 coupled to a position indicator 430. The position indicator can, for example, comprise a stroboscope disc which cooperates with a photoelectric barrier, the output of the photoelectric barrier being connected to a counter. The output signal from the position indicator 430 is thus unambiguously associated with the position of the z-shaped carriage 422.

The z-shaped carriage 422 carries, for its part, two guide rods 432, 434 passing in holes 436, 438 in a y-shaped carriage 440. The y-shaped carriage is also provided with a tapped hole 442 in which there passes a threaded spindle 444. The threaded spindle is driven by an electric motor 446 which is locked to a position indicator 448. The construction of the position indicator 448 is identical to that of the position indicator 430.

The y-shaped carriage 440 carries two guide rods 450, 452 which pass in holes 454, 456 in an x-shaped carriage 458. The x-shaped carriage is provided with a tapped hole 460 in which there passes a threaded spindle 462. The threaded spindle is driven by an electric motor 464 to which a position indicator 466 is, again, flanged.

The x-shaped carriage 458 provides support for a patient's chin and is provided with a thin resilient rest 468.

As will be apparent from the foregoing description, the various carriages and the electric motors driving them allow the rest 468 to be adjusted in the x, y and z directions. Mounted on the underside of the x-shaped carriage 458 is a shaft 470 which is rigidly connected to a pivot arm 472. The pivot arm 472 carries on the upper side of its outermost portion a length-variable strut 474 which extends in the z direction and the length of which can be adjusted by an associated electric motor 476. The electric motor 476 is, again, locked to a position indicator 478.

The upper end of the strut 474 carries a contact probe 480 which is configured in the manner of a spring cylinder. A palpation probe 482 biased by the spring carries at its free end a free-running roll 484 which revolves about a vertical axis. The axial dimensions of the roll 484 are such that it is slightly smaller than the midway point of average teeth. The diameter of the roll 484 is such that it travels easily on the outside of the soft tissue covering the dental arch.

The contact probe 480 further comprises a position indicator 486 which establishes the position of the palpation probe 482.

For pivoting the contact probe 480 beyond the dental arch 68, there is coupled to the shaft 460 an electric motor 488 which is locked to a position indicator 490.

The various position indicators 430, 448, 466, 478 and 490 are each identical in their construction. The position indicator 486 can in principle have a similar construction if its input shaft is provided with a pinion which cooperates with a rack formed on the palpation probe 482. Alternatively, the position indicator 486 can also comprise a photoelectric barrier which cooperates with a ruled grating moved by the palpation probe 482.

The output signals from the various position indicators are connected to inputs of a control unit 492 which also has outputs at which control signals for the electric motors 428, 446, 464, 476 and 488 are provided.

The device shown in FIG. 9 allows the actual position and the actual shape of the dental arch 68 to be measured in a panorama X-ray apparatus 10.

For this purpose, the rest 468 is firstly positioned, by appropriate activation of the electric motors 428, 446 and 464, in such a way that the dental arch is located in the recording plane E.

The patient's head is then held in the recording plane. Activation of the electric motor 476 then causes the strut 474 to be extended sufficiently far for the roll 484 of the contact probe 480 to be located at the same height as the dental arch or jaw to be examined.

The electric motor 488 is then excited in such a way that the pivot arm 472 is rotated through 180°. During this movement, the roll 484 follows, under the force of the biased spring of the contact probe 480, the outer contour the dental arch or the jaw.

The corresponding output signals from the position indicator 486 are stored, together with the output signals from the position indicator 490, in the control unit 492.

The control unit accordingly then contains, in digital form, the actual outer contour and actual position of the jaw or dental arch. Via the output signals from the position indicators 448 and 466, the control unit 492 also knows the absolute position of the dental arch in the x-y plane, and adding the output signals from the position indictor 430 and the position indicator 478 also discloses the z coordinate of the dental arch. This should correspond to the z coordinate of the recording plane E.

In a simplified embodiment of the device, the z-shaped carriage 422 and the y-shaped carriage 440 can also be omitted and there be provided merely the carriage 458 which is then adjustable merely in the vertical direction, either manually or by a servomotor.

The control unit 492 calculates on the basis of the dental arch, measured as described hereinbefore, that path 84 on which the axis A has to be moved in the x-y plane to make the projection arch surface 88 of the panorama X-ray apparatus 10 coincide with the measured dental arch. Corresponding control signals are passed onto the coordinate drive 30-$x$ acting in the x direction and the coordinate drive 30-$y$ acting in the y direction which together adjust the position of the axis A in the x-y plane.

The materials of the components located in the ray path between the X-ray source and CCD sensor 16, i.e. the positioning device 50 and also the sensors 58, 92 and 98, 100, consist substantially of materials displaying low X-ray absorption, in particular plastics materials.

The jaw form identification circuit 62 referred to in the aforementioned embodiments can also be one of the actual components of the corresponding computing unit 32 or a program running thereon, so the respective sensors 58, 92 and 98, 100 transmit their respective output signals directly to the computing unit 32.

The sensors 58, 92 and 98, 100 are also capable of establishing a patient's dental arch without the patient being held in the positioning device 50. Only once his dental arch has been determined outside the panorama X-ray apparatus 10 is the patient then brought into the correspondingly calculated set relative position.

The dental arch can also be determined by the sensors 58, 92 and 98, 100 without the patient having to be present. This is the case, for example, if there is an imprint of the patient's jaw which can then be detected by the corresponding sensor like a natural jaw and can be examined.

It is to be understood that additional embodiments of the invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A method for determining the set relative position of a patient in a dental panorama X-ray apparatus, the method comprising:
   establishing the curvature of a front region of a patient's dental arch;
   establishing the curvature of a central region and/or a rear region of the patient's dental arch; and calculating set position coordinates for the patient's jaw based on the established curvature of the front region and the central and/or rear region of the patient's dental arch and on a projection arch surface of the panorama X-ray apparatus.

2. A method for determining the set path on which a dental panorama X-ray apparatus is moved with respect to a patient, the method comprising:

establishing the curvature of a front region of a patient's dental arch fixing the patient's dental arch at a location in the panorama X-ray apparatus located within the space scanned by an X-ray source and a detector unit connected rigidly thereto, establishing, the curvature of a central region and/or rear region of the patient's dental arch; and, based on the measured curvatures of the front and central and/or rear region of the dental arch, calculating a set path curve for a diagnostic unit including the X-ray source and detector unit, the calculated set path curve being dependent on the measured curvatures of the front, central, and/or rear region of the dental arch.

3. A device for determining the set relative position of a patient in a dental panorama X-ray apparatus or the set path of a diagnostic unit with respect to the patient's jaw fixed in the panorama X-ray apparatus, the device comprising:

a sensor unit which cooperates with the patient's teeth in the front region of the jaw and with the patient's teeth in the central and/or rear region of the jaw and which generates a jaw form signal characteristic of the position of the patient's teeth relative to one another;

a projection arch surface which is defined by the path of an X-ray source and a detector unit of the panorama X-ray apparatus; and a computing unit that receives the jaw form signal from the sensor unit and which calculates the set position coordinates for the patient's jaw based upon the jaw form signal and the projection arch surface.

4. The device according to claim 3, wherein
the sensor unit comprises at least one sensor and a jaw identification circuit which communicates therewith and generates a jaw form signal which corresponds to the sensor output signal and is characteristic of the geometry of the patient's dental arch.

5. The device of claim 4, wherein
the jaw identification circuit is integrated into the computing unit.

6. The device of claim 3, wherein
the sensor unit comprises a bite-on sensor arranged on a bite-on holder of the panorama X-ray apparatus.

7. The device of claim 6, wherein
the bite-on sensor comprises a plurality of pressure transducers on a side facing the patient's upper jaw and/or lower jaw.

8. The device of claim 3, wherein
the sensor unit comprises a movable probe tip and a position indicator arrangement indicating the position thereof.

9. The device of claim 8, wherein
the sensor is movable in a direction perpendicular to the probing direction and a further position indicator establishes the position of the sensor in the direction of movement.

10. The device of claim 3, wherein
the sensor unit comprises at least one camera which is arranged so as to produce an image of the patient's jaw.

11. The device of claim 3, wherein
the sensor unit includes materials displaying low X-ray absorption.

12. The device of claim 3, wherein the sensor unit consisting substantially of materials displaying low X-ray absorption.

* * * * *